(12) United States Patent
Kelley et al.

(10) Patent No.: US 7,951,479 B2
(45) Date of Patent: May 31, 2011

(54) METHOD AND APPARATUS FOR POROUS INSULATIVE FILM FOR INSULATING ENERGY SOURCE LAYERS

(75) Inventors: Shawn Kelley, Shoreview, MN (US); Tom E. Notebaart, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1477 days.

(21) Appl. No.: 11/127,025

(22) Filed: May 11, 2005

(65) Prior Publication Data
US 2006/0257726 A1   Nov. 16, 2006

(51) Int. Cl.
*H01M 6/00* (2006.01)
*H01M 2/14* (2006.01)
*H01M 2/18* (2006.01)

(52) U.S. Cl. ......... 429/122; 429/129; 429/139; 429/130

(58) Field of Classification Search ................ 429/122, 429/139, 249, 129, 130
See application file for complete search history.

(56) References Cited

U.S. PATENT DOCUMENTS

| | | |
|---|---|---|
| 3,201,280 A | 8/1965 | Yumoto |
| 4,113,921 A | 9/1978 | Goldstein et al. |
| 4,169,003 A | 9/1979 | Dangel et al. |
| 4,200,687 A | 4/1980 | Frode et al. |
| 4,232,099 A | 11/1980 | Sullivan |
| 4,659,636 A | 4/1987 | Suzuki et al. |
| 4,663,253 A | 5/1987 | Simonton et al. |
| 4,849,144 A | 7/1989 | McLoughlin |
| 4,937,154 A | 6/1990 | Moses et al. |
| 4,952,864 A * | 8/1990 | Pless et al. ............... 323/299 |
| 5,116,698 A | 5/1992 | Sears |
| 5,360,684 A | 11/1994 | Duval et al. |
| 5,415,959 A | 5/1995 | Pyszczek et al. |
| 5,439,760 A | 8/1995 | Howard et al. |
| 5,458,993 A | 10/1995 | Terao et al. |
| 5,486,215 A | 1/1996 | Kelm et al. |
| 5,503,948 A | 4/1996 | MacKay et al. |
| 5,549,717 A | 8/1996 | Takeuchi et al. |
| 5,628,801 A | 5/1997 | MacFarlane et al. |
| 5,631,102 A * | 5/1997 | Spillman et al. ........... 429/94 |

(Continued)

FOREIGN PATENT DOCUMENTS

JP     58192271     11/1983

(Continued)

OTHER PUBLICATIONS

Haasl, Benjamin J., et al., "Insulative Member on Battery Cathode", U.S. Appl. No. 11/140,854, filed May 31, 2005, 30 Pages.

(Continued)

*Primary Examiner* — Helen O Conley
(74) *Attorney, Agent, or Firm* — Schwegman, Lundberg & Woessner, P.A.

(57) ABSTRACT

The present subject matter includes an apparatus, having: an anode having an elongate ribbon shape; a cathode having an elongate ribbon shape, the cathode disposed adjacent to and in alignment with the anode; a separator disposed between the anode and the cathode; and a first porous edge film disposed between a first edge of the cathode and the anode, with the one or more surfaces of the first porous edge film facing the cathode and defining a first cathode interface of the first porous edge film; wherein an first adhesive interconnects the first porous edge film to the cathode, the first adhesive covering less than the entire cathode interface, and the anode and cathode are disposed in a case with an electrolyte.

17 Claims, 2 Drawing Sheets

U.S. PATENT DOCUMENTS

| | | | |
|---|---|---|---|
| 5,741,608 A * | 4/1998 | Kojima et al. | 429/94 |
| 6,190,426 B1 | 2/2001 | Thibault et al. | |
| 6,225,778 B1 | 5/2001 | Hayama et al. | |
| 6,330,925 B1 | 12/2001 | Ovshinsky et al. | |
| 6,699,265 B1 | 3/2004 | O'Phelan et al. | |
| 6,869,654 B2 | 3/2005 | Ginkel et al. | |
| 2003/0165744 A1 | 9/2003 | Schubert et al. | |
| 2004/0127952 A1 | 7/2004 | O'Phelan et al. | |
| 2006/0023400 A1 | 2/2006 | Sherwood | |
| 2006/0035152 A1 * | 2/2006 | Nishimura et al. | 429/234 |

FOREIGN PATENT DOCUMENTS

| | | | |
|---|---|---|---|
| WO | WO2004/062022 | * | 7/2004 |

OTHER PUBLICATIONS

O'Phelan, Michael J., et al., "Batteries Including a Flat Plate Design", Provisional U.S. Appl. No. 60/437,537, filed Dec. 31, 2002, 116 Pages.

Sherwood, Gregory J., "Method and Apparatus for High Voltage Aluminum Capacitor Design", U.S. Appl. No. 11/182,707, filed Jul. 15, 2005, 239 Pages.

Sherwood, Gregory J., "Method and Apparatus for Providing Flexible Partially Etched Capacitor Electrode Interconnect", Provisional U.S. Appl. No. 60/588,905, filed Jul. 16, 2004, 241 Pages.

"U.S. Appl. No. 11/140,854, Restriction Requirement mailed Mar. 19, 2009", 9 pgs.

"U.S. Appl. No. 11/140,854, Non-Final Office Action mailed Aug. 31, 2009", 6 pgs.

"U.S. Appl. No. 11/140,854, Advisory Action mailed Jul. 16, 2010", 3 pgs.

"U.S. Appl. No. 11/140,854, Final Office Action mailed May 11, 2010", 11 pgs.

"U.S. Appl. No. 11/140,854, Response filed Jul. 12, 2010 to Final Office Action mailed May 11, 2010", 16 pgs.

* cited by examiner

METHOD AND APPARATUS FOR POROUS INSULATIVE FILM FOR INSULATING ENERGY SOURCE LAYERS

CROSS REFERENCE TO RELATED APPLICATIONS

The following commonly assigned U.S. patent is related to the present application and is incorporated herein by reference in its entirety: "Flat Capacitor for an Implantable Medical Device," U.S. Pat. No. 6,699,265, filed Nov. 3, 2000, issued Mar. 2, 2004. The present application is related to the following commonly assigned U.S. Patent Publications which are incorporated herein by reference in their entirety: "Method and Apparatus for Single High Voltage Aluminum Capacitor Design," Ser. No. 60/588,905, filed on Jul. 16, 2004; "Batteries Including a Flat Plate Design," Ser. No. 10/360,551, currently U.S. Pat. No. 7,479,349, filed Feb. 7, 2003, which claims the benefit under 35 U.S.C 119(e) of U.S. Provisional Application Ser. No. 60/437,537 filed Dec. 31, 2002.

TECHNICAL FIELD

This disclosure relates generally to self-contained energy sources, and more particularly to method and apparatus for porous insulative film for insulating energy source layers.

BACKGROUND

Energy storage components, such as batteries and capacitors, are used in a variety of electronic devices. As technology evolves, devices using these components consistently demand smaller component sizes. However, in meeting the demands of technology, these components cannot sacrifice performance. As such, the art requires energy storage components which are smaller, but which meet or exceed energy requirements.

In meeting these requirements, energy storage components have their own requirements, extending to manufacturing, use, and end of life performance. Manufacturing requirements demand reliable and efficient assembly. Use requirements demand reliability and small package sizes having satisfactory power delivery. End of life requirements require that as the components age, they retain their operable characteristics. Within each of these phases is the demand that battery subcomponents are not damaged by other battery subcomponents. Thus, what is needed are new energy storage subcomponent designs which demonstrate improved properties with respect to manufacturing, use, and end of life, without damaging other subcomponents.

SUMMARY

The above-mentioned problems and others not expressly discussed herein are addressed by the present subject matter and will be understood by reading and studying this specification.

One embodiment of the present subject matter includes an apparatus, having: an anode having an elongate ribbon shape; a cathode having an elongate ribbon shape, the cathode disposed adjacent to and in alignment with the anode; a separator disposed between the anode and the cathode; and a first porous edge film disposed between a first edge of the cathode and the anode, with the one or more surfaces of the first porous edge film facing the cathode and defining a first cathode interface of the first porous edge film; wherein an first adhesive interconnects the first porous edge film to the cathode, the first adhesive covering less than the entire cathode interface, and the anode and cathode are disposed in a case with an electrolyte.

Additionally, in one embodiment, the present subject matter includes an apparatus having an anode including alkali metal and having an elongate ribbon shape; a cathode including metal oxide conformed to a wire mesh substrate, the cathode having an elongate ribbon shape having a cathode width and an cathode length, the cathode length extending between a first and second cathode edge, a separator including porous polymeric material disposed between the anode and the cathode; a first and second porous edge film including porous polymeric materials, the first and second porous edge films respectively wrapped around the first and second cathode edges, with one or more surfaces of the first and second porous edge films facing the cathode and defining a first and second respective cathode interface; a battery case having a first opening sized for passage of the anode, the cathode, the separator, and the first and second porous edge films, the battery case having a feedthrough and an electrolyte backfill port; a battery case lid sealably conformed to the first opening of the battery case; pulse generation electronics electrically connected to the anode and the cathode; and a hermetically sealed device housing having a device housing opening sized for passage of the battery case and the pulse generation electronics, with a housing lid sealably conformed to the device housing opening; wherein a pressure sensitive adhesive interconnects the first and second porous edge films to the cathode along less than the entire first and second cathode interfaces, and the anode, cathode, separator and first and second porous edge films are disposed in a jelly roll configuration in the battery case along with electrolyte, with the battery case and the pulse generation electronics disposed in the hermetically sealed device housing.

One embodiment of the present subject matter includes an apparatus, having: an anode having an elongate ribbon shape; a cathode having an elongate ribbon shape, the cathode disposed adjacent to and in alignment with the anode; a separator disposed between the anode and the cathode; and an edge film means for insulating the edge of the cathode from the anode.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

Figure 1:
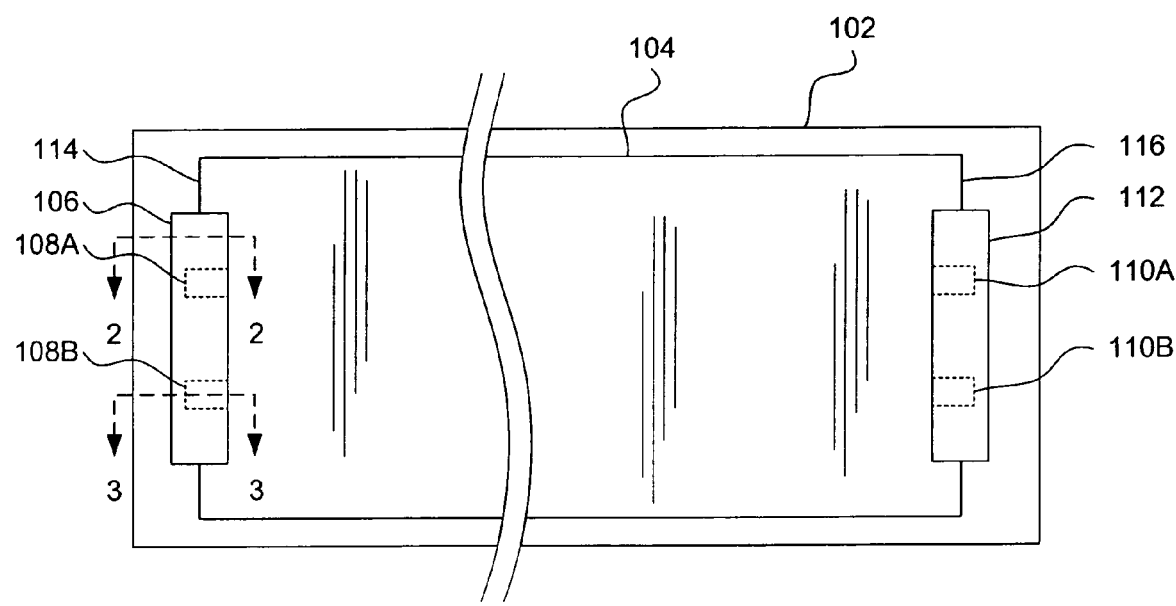
FIG. 1 is a top view including an anode and a cathode, according to one embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Self-powered electronic devices are known. For example, implantable medical devices are now in use for treating a variety of diseases. Some implantable pulse generation devices, as well as other types of implantable medical devices, are powered by a battery contained within the housing of the device. Additional designs include, within the housing of the device, a capacitor sized to deliver a pulse of a selected intensity and duration. Various designs couple batteries and capacitors to achieve desired function. The present subject matter is related to batteries and capacitors for these devices.

Batteries within the scope of the present subject matter include various subcomponents. For example, various battery embodiments include opposing anode and cathode plates. Because of pressure to reduce battery size in order to make electronic devices smaller, various configurations using these plates are employed. Some embodiments of the present subject matter use elongate ribbon shaped plates which are adjacent and parallel, and which are wound together lengthwise to form a roll. Plates are rolled for various reasons. One reason is to increase packaging efficiency. Another reason is to increase manufacturing efficiency.

Various embodiments utilize anode and cathode designs which require separators to electrically isolate the anode and the cathode. Some separators, in various embodiments, include porous materials to promote the spread of electrolyte to the anode and the cathode. In some embodiments, separators include additional features, such as an ability to melt in response to thermal input, substantially canceling the porous nature of the separator. It is necessary to ensure that separators are not damaged, as damaged separators will not function as designed.

Various embodiment of the present subject matter utilize ribbon shaped electrodes which include edge features which can damage separators. These features can damage other components as well. In some embodiments, an electrode includes wire mesh substrate which has been excised from a larger portion of wire mesh. In some embodiments, along the excised edge(s), the wire mesh has sharp features. The present subject matter provides a covering for positioning between these sharp features and additional subcomponents, to protect those subcomponents. In one embodiment of the present subject matter, the covering is wrapped around the excised edge.

In various embodiments, the excised edge covering is a film. In some embodiments, the film is porous. In some electrochemical embodiments, a porous film is useful to promote the spread of electrolyte between the anode and the cathode. In various embodiments, the film additionally has an adhesive which interconnects the film to the electrode. Some embodiments of the present subject matter use a non-porous adhesive. In some of these embodiments, the adhesive is configured along the film in a pattern which covers less than the entire film. The present subject matter covers these embodiments, but is not limited to these embodiments.

FIG. 1 is a top view including an anode and a cathode, according to one embodiment of the present subject matter. The embodiment includes an anode layer 102, and a cathode layer 104. Also pictured is first edge film 106 and a second edge film 112. Additionally pictured in hidden lines are adhesives 108A-B, 110A-B.

The pictured embodiment is substantially planar, having a planar anode 102 disposed along a planar cathode 104. Various embodiments, however, include anodes and cathodes which are wound together into a roll. For example, in one embodiment, the electrodes are wound in a direction extending from the first edge film 106 to the second edge film 112. Winding can benefit manufacturing processes by decreasing the time needed to create a small package size power cell.

Winding, in various embodiments, introduces a tension in the winding materials. This tension is the product of winding the roll tightly. This tension has a tendency to push adjacent components together. For example, in a wound embodiment, first edge 114 of cathode 104 is pushed against anode 102. In various embodiments, the introduction of this tension, and the disposition of the first edge 114 against anode 102, requires provisions to improve design reliability such that first edge 114 does not damage anode 102.

For example, in various embodiments, anode 102 and cathode 104 are separated by a separator. In various embodiments the separator substantially encapsulates the anode 102, but other designs are within the scope of the present subject matter. The present subject matter includes, but is not limited to, separators illustrated in paragraphs 0175-0179 of related and commonly assigned U.S. patent publication, "Batteries including a flat plat design," U.S. Patent Publication No. 2004/0127952, filed Feb. 7, 2003, incorporated herein by reference. The separator, in various embodiments, is disposed between the anode 102 and the cathode 104 proximal first edge 114, and first edge 114 is pressed against the separator.

In various embodiments, cathodes have a wire mesh substrate. In some of these embodiments, the cathode 104 is excised from the wire mesh substrate. In excising the cathode from the wire mesh substrate, various embodiments create edges which have burrs. Additional edges have sharp features which are not burrs, such as wire portions which protrude. In some of these embodiments, the sharp features of the cathode edge 114 are pushed against the separator. In the pictured example, sharp features are limited to a first cathode edge 114 and a second cathode edge 116, due, in part, to manufacturing processes which produce a strip of wire mesh which has edges extending lengthwise along the strip which do not have sharp features. In this process, the cathode 104 is excised from the strip along edges 114 and 116. This process serves to illustration the present subject matter, but other configurations also exist within the scope of the present subject matter.

To reduce instances of separator damages from cathode edges 114, 116 contacting a separator, various embodiments include edge films 106, 112. Edge films 106, 112, in various embodiments, include materials which are of increased toughness such that the films do not tear when contacted by a cathode edge 114. In additional embodiments, edge films 106, 112 have a thickness adapted to prevent damage. By disposing edge films 106, 112 between cathode edges 114, 116, damage from the cathode can be limited. While the pictured embodiment uses edge films which do not extend completely along cathode edge 114, additional embodiments feature edge films which do. Still further embodiments provide edge films which extend beyond the boundaries of cathode edge 114.

Damage extends to damaging separators, but also extends to other forms of damage, such as shorting, breakdown, or disruption of electrode materials. For example, in some embodiments, the anode is comprised of a pellet. High point loads against the pellet can encourage the pellet to lose its shape, in some embodiments. Additional embodiments have a brittle oxide coating which can be disrupted by areas of high stress. Edge films 106, 112 work to reduce these types of disruptions. Edge films 106, 112 also produce other features, including stability in use and during manufacturing. For example, edge films 106, 112 assist during winding of anode 102 and cathode 104, by providing a smooth surface for those layers to traverse, without catching or snagging.

Figure 2:
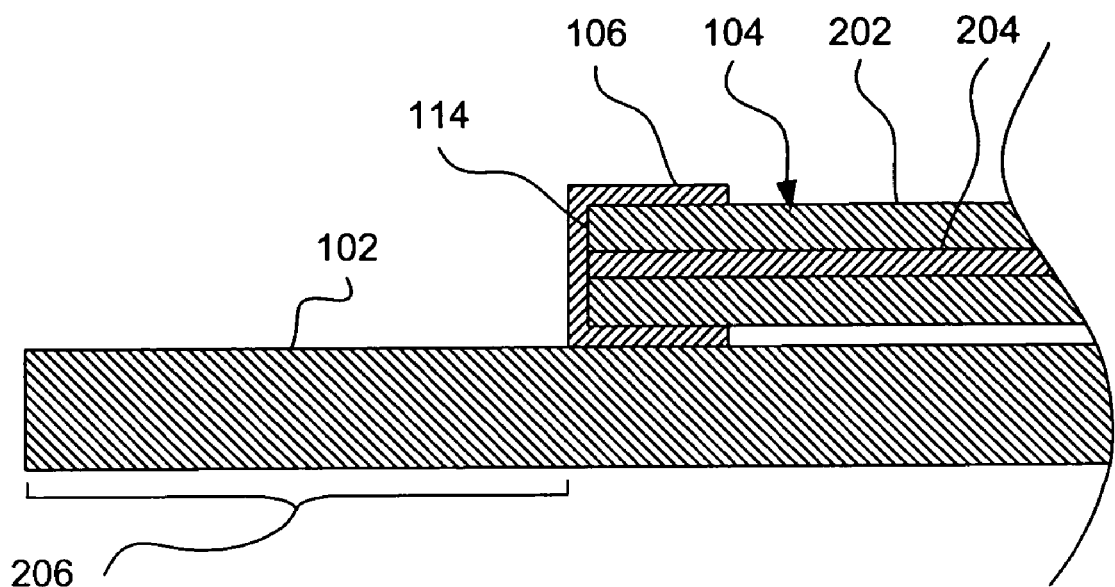
FIG. 2 is a partial side view taken at line "2" of FIG. 1, according to one embodiment of the present subject matter.

FIG. 2 is a partial side view taken at line "2" of FIG. 1, according to one embodiment of the present subject matter. The illustration shows an edge film 106 wrapped around the edge 114 of cathode 104. Additionally visible is a cathode material 202 and a cathode substrate 204, to which the cathode material 202 is affixed. Anode 102 is additionally pictured.

The cathode material 202 can include a metal, a metal oxide, a mixed metal oxide, a metal sulfide and carbonaceous materials. For example, various embodiments include carbon, fluorinated carbon, silver vanadium oxide, copper silver vanadium oxide, copper vanadium oxide, manganese dioxide, cobalt oxide, nickel oxide, copper oxide, iron sulfide, iron disulfide and others. Additionally, various binder materials may be used in cathode material 202, including fluoro-resin powders such as polytetrafluoroethylene (PTFE) powder and materials having electronic conductive characteristics such as graphite and/or carbon black. In some cases, no binder material or electronic conductor material is used. These materials provide examples of cathodic materials, but the present subject matter is not so limited.

In various embodiments, cathode materials 202 are affixed to a substrate 204. For example, in one embodiment, a cathode 104 is prepared by using pressure to affix cathode materials 202 to a substrate 204. The substrate 204, in various embodiments, functions as a current collector. Example substrates include titanium, stainless steel and nickel. Alloys including multiple examples of these elements are also possible. Terminal portions extending away from the substrate are also possible.

In various embodiments, the substrate 204 may have sharp features proximal edge 114. To prevent these features from contacting other battery components, edge film 106 is used, in various embodiments. In the pictured embodiment, the edge film 106 is wrapped around edge 114. In various embodiments, an anode overhang 206 may be wrapped around the cathode edge 114. In embodiments where an anode overhang 206 is wrapped around the cathode edge 114, the positioning of the edge film 106 around edge 114 provides protection for the anode 102 from sharp features present at cathode edge 114. However, in additional embodiments, the anode 102 and cathode 104 are not wrapped as such. Additional embodiments include an edge film 106 which is disposed between the anode 102 and the cathode 104 without wrapping around edge 114.

In various embodiments, the anode includes an alkaline metal, such as lithium. Various alloys which serve as anodes are within the scope of the present subject matter, including LiSi, LiAl, LiB, LiMg, LiAlMg, and LiSiB. These materials provide examples of anodic materials, but the present subject matter is not so limited.

Edge film 106, in various embodiments, is compatible with electrode chemical activity between anode 102 and cathode 104. For example, in various embodiments, edge film 106 is chemically unreactive with anode 102 and cathode 104. Additionally, in various embodiments, edge film 106 is porous. For example, various embodiments include porosity sufficient to allow electrolyte to flow through the edge film 106, with the electrolyte extending to the anode 102 and the cathode 104. Illustrative materials for the edge film 106 include various polymers. Some edge films have microporous properties. Various films include polyethylene tetrafluoroethylene (PETFE). Some embodiments include polypropylene membrane available under the brand name CELGARD, a product of Celgard LLC, of Charlotte, N.C. Additional embodiments include non-woven glass and glass fiber materials, woven glass fiber materials, polypropylene, polyethylene, microporous materials, ceramics, polytetrafluoroethylene membrane, polypropylene membrane, and woven separators having halogenated polymeric fibers. Although the edge film is shaped like a thin sheet, additional embodiments having alternation shapes adapted for disposition between an electrode edge and another electrode fall within the scope of the present subject matter.

Figure 3:
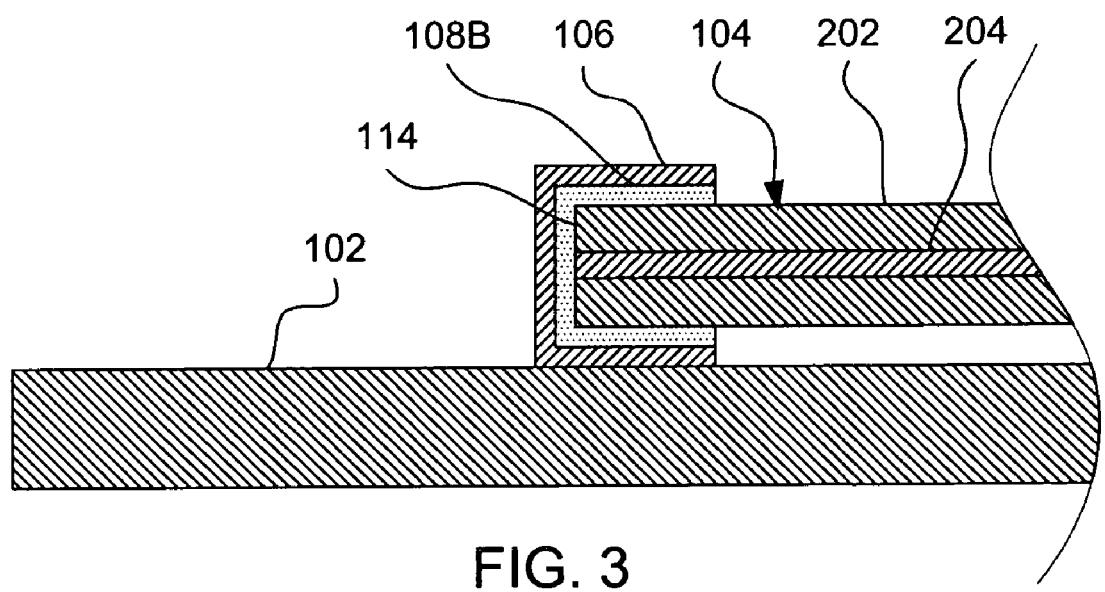
FIG. 3 is a partial side view taken at line "3" of FIG. 1, according to one embodiment of the present subject matter.

FIG. 3 is a partial side view taken at line "3" of FIG. 1, according to one embodiment of the present subject matter. The illustration shows an edge film 106 wrapped around the edge 114 of cathode 104. Additionally visible is a cathode material 202 and a cathode substrate 204, to which the cathode material 202 is affixed. Anode 102 is additionally pictured. Additionally pictured is adhesive 108B.

In various embodiments, the present subject matter includes an adhesive on at least one surface for the purpose of adhering the edge film to a surface. Although the illustration shows the edge film 106 wrapped around a cathode edge 114, other embodiments are possible. The edge film may alternately be wrapped around an edge of an anode, for example. The edge film may additionally be disposed between a cathode and an anode without wrapping.

In various embodiments, the adhesive 108B is a pressure sensitive adhesive (PSA). In some embodiments, the PSA is covered by a release liner. In various embodiments, during the assembly of the edge film, prior to bonding the edge film to a surface, the PSA is applied to the edge film using a release liner. In additional embodiments, the PSA is applied to a target surface, such as the cathode edge, using a release liner. The PSA may additionally be applied to the anode. The PSA does not necessarily have to wrap around an edge; embodiment disposing the PSA between the cathode and the anode at one of a cathode edge or an anode edge fall within the scope of the present subject matter. In various embodiments, the release liner is a paper or plastic film material having a release coating.

In one embodiment, a surface of the edge film facing a target surface is covered by the adhesive, and the remainder of the edge film face is exposed. For example, in various embodiments, it is possible to trace a path across the surface of the edge film to which the adhesive is adhered, without encountering the adhesive. In some of these embodiments, the path is a substantially straight line. In one embodiment, in which the edge film is elongate and applied to the short edge of an elongate ribbon shaped cathode, the path extends across the edge film such that it is substantially straight and substantially perpendicular to the length of the ribbon shaped cathode.

The organization of adhesive on the edge film as such is for several reasons. In some battery embodiments, the adhesive is organized as such so that lithium is depleted from the anode in a manner which does not short or truncate the lithium electrode. For example, in various embodiments, a sheet of cathode lies on a sheet of anode. In some of these embodiments, at least one edge film is disposed between at least one cathode edge and the anode. If this edge film were nonporous, in various embodiments, the lithium in the penumbra of the interface between the anode and the edge film would deplete at a higher rate. This is because the potential between the anode portion defined by the edge film perimeter and the cathode portion defined by the edge film perimeter remains, while the ion paths for that potential are all bent around the edge film. As such, the penumbra of the edge film interface includes more ion paths per unit of area than do other portions of the battery not having a non-porous edge film. More ion paths mean faster depletion.

If the edge film extended across a width of the lithium sheet, this depletion would effectively truncate a portion of the lithium anode that extended outside the perimeter of the cathode. To resist this behavior, various configurations use a porous edge film, a configuration which has the tendency of regularizing the rate of lithium depletion in areas proximal the edge film. But, to fulfill various manufacturing efficiency needs, in various embodiments edge film is be adhered to at least one of the anode and the cathode. In various embodiments, the adhesive is nonporous. This reintroduces the truncation problem, in various embodiments.

As such, the present subject matter includes configurations which ensure one or more paths extend across the edge film which do not have adhesive. By limiting the high-depletion rate areas of the anode to less than the entire width of the anode, various embodiments of the present subject matter reduce the tendency for truncation of a portion of the anode which extends outside the perimeter of the cathode. This reduction in truncation allows for improved end-of-life behavior of the battery.

Although the present example includes a film-type PSA, it should be noted that other embodiments fall within the scope of the present subject matter. Adhesives which have the tendency of adhering the cathode to the edge film, or the anode to the edge film, fall within the scope of the present subject matter. This includes spray-on adhesives. This additionally includes adhesives applied in striped patterns, in half-tone patterns, or in other patters. Additional types of patterns are within the scope of the present subject matter. Additional adhesive application methods fall within the scope of the present subject matter.

Returning to the discussion of PSA, it is noted that various embodiments may be derived from a variety of known water-based, solvent-based, and 100% solids hot melt adhesive compositions. In various embodiments, adhesive compositions are selected depending on the intended duration of use and expected exposure conditions of the edge film (e.g. temperature, humidity, sunlight, delamination). Transparent adhesive compositions, translucent and opaque adhesive compositions fall within the scope of the present subject matter. Colored adhesives additionally fall within the scope of the present subject matter. One type of adhesive is commercially available from 3M Company, organized in St. Paul, Minn., under the trade designation 200 MP.

In various embodiments, the present invention includes PSAs including alkylacrylate polymers and copolymers; copolymers of alkylacrylates with acrylic acid; terpolymers of alkylacrylates, acrylic acid, and vinyl-lactates; alkyl vinyl ether polymers and copolymers; polyisoalkylenes; polyalkyldienes; alkyldiene-styrene copolymers; styrene-isoprene-styrene block copolymers; polydialkylsiloxanes; polyalkylphenylsiloxanes; natural rubbers; synthetic rubbers; chlorinated rubbers; latex crepe; rosin; cumarone resins; alkyd polymers; and polyacrylate esters and mixtures thereof. Additionally, the present subject matter includes polyisobutylenes, polybutadienes, or butadiene-styrene copolymers, and mixtures thereof; silicone-based compounds such as polydimethylsiloxane, and polymethylphenylsiloxane combined with other resins and/or oils. The present subject matter further includes terpolymers of ethyl acrylate, butyl acrylate, and acrylic acid; copolymers of isooctylacrylate and acrylamide; and terpolymers of isooctylacrylate, vinyl-acetate, and acrylic acid. In various embodiments, acrylic-based PSAs are coated by an organic solvent, such as a heptane:isopropanol solvent mixture, which is later evaporated. Additionally PSAs within the scope of the present subject matter include tackified thermoplastic resins and tackified thermoplastic elastomers, wherein the tackifier comprises one or more compounds which increase the tack of the composition. While the present subject matter includes these materials, additional materials can be selected, and additional combinations of these materials fall within the scope of the present subject matter.

As such, a method within the scope of the present subject matter includes applying an adhesive to a porous edge film in a pattern; applying the porous edge film to an edge of an elongate cathode having a ribbon shape such that the adhesive adheres the porous edge film to the edge of the cathode, with the one or more surfaces of the porous edge film which face the cathode being partially covered by adhesive; disposing the cathode adjacent an anode having an elongate ribbon shape, with a separator disposed between the anode and the cathode, such that the porous edge film is disposed between the anode and the cathode; and disposing the anode, the cathode, the separator, and the porous edge film in a case, with electrolyte disposed in the case. Some of these methods include rolling the anode and the cathode together.

APPLICATION

In various applications, the anode 102, cathode 104, along with an electrolyte and associated components are assembled for use as an energy source. In various embodiments, the anode and cathode are wound together. In additional embodiments, they are otherwise folded together. In some embodiments, they are not wound. Various embodiments include a stack of planar electrodes. Each of these embodiments is combined with a respective case for use. In various embodiments a case includes one or more terminal feedthroughs for interconnecting electrodes to components separate from the energy source. A case may be conductive, in various embodiments. In some of these embodiments, the case is interconnected with electrodes, and is active. Various embodiments include within the case an electrolyte. Some of these embodiments includes a backfill port for filling the case with electrolyte.

In various embodiments, the energy source case is disposed in a device housing. The device, in various embodiments, includes a capacitor for providing power for pulse generation. In various embodiments, electronics are disposed in the housing. In some embodiments, a battery, a capacitor, and electronics are disposed in a sealed housing adapted for implantation. The housing, in various embodiments, is hermetically sealed. Some embodiments include interface features, such as sealed connectors, for interconnecting the device to additional components. In one embodiment, leads for disposition in vasculature are interconnected to the device. Some embodiments use the leads in conjunction with the device housing to generate an electronic potential.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. An apparatus, comprising:
an anode having an elongate ribbon shape;
a cathode having an elongate ribbon shape, the cathode disposed adjacent to and in alignment with the anode;
a separator disposed between the anode and the cathode; and
a first porous edge film disposed against a cathode first surface, the first porous edge film further disposed around and onto an opposed second cathode surface defining a cathode and separator interface, with the first porous edge film disposed against the separator wherein the first porous edge film protects the separator from contacting an conductive surface of the cathode along the first edge of the cathode and protects the cathode from tearing the separator and contacting the anode,
wherein a first adhesive interconnects the first porous edge film to the cathode, the first adhesive covering less than the entirety of the cathode interface, and the anode and cathode are disposed in a case with an electrolyte, and wherein the first adhesive is disposed along the first porous edge film such that one or more areas of the first porous edge film are not covered with the first adhesive.

2. The apparatus of claim 1, wherein the first adhesive is a pressure sensitive adhesive.

3. The apparatus of claim 1, wherein the anode includes an alkali metal.

4. The apparatus of claim 1, wherein the cathode includes a metal oxide.

5. The apparatus of claim 4, wherein the electrolyte includes an organic compound.

6. The apparatus of claim 1, wherein the first porous edge film includes polyethylene tetrafluoroethylene.

7. The apparatus of claim 6, wherein the first porous edge film has a porosity of approximately 55%.

8. The apparatus of claim 1, where the anode and the cathode are arranged in a jelly roll.

9. The apparatus of claim 8, where the anode and the cathode are connected to respective terminals which are interconnected to pulse generation electronics, the pulse generation electronics and case disposed in an hermetically sealed implantable device housing.

10. The apparatus of claim 1, wherein the cathode has the shape of an elongate body extending lengthwise between the first edge and a second edge, and the first porous edge film is wrapped around the first edge of the cathode.

11. The apparatus of claim 10, wherein the first adhesive is striped along the first porous edge film such that one or more areas of the first porous edge film are not covered with the adhesive in a direction parallel a direction extending between the first and second edge of the cathode.

12. The apparatus of claim 1, further comprising a second porous edge film disposed between a second edge of the cathode and the anode, with the one or more surfaces of the second porous edge film facing the cathode and defining a second cathode interface of the second porous edge film.

13. The apparatus of claim 12, wherein the second porous edge film is wrapped around a second edge.

14. The apparatus of claim 12, wherein a second adhesive interconnects the second porous edge film to the cathode, the second adhesive covering less than the entirety of the cathode interface.

15. An apparatus, comprising:
an anode including alkali metal and having an elongate ribbon shape;
a cathode including metal oxide conformed to a wire mesh substrate, the cathode having an elongate ribbon shape having a cathode width and an cathode length, the cathode length extending between a first and second cathode edge,
a separator including porous polymeric material disposed between the anode and the cathode;
a first and second porous edge film including porous polymeric materials, the first and second porous edge films respectively disposed against each the first and second cathode edges, one or more surfaces of the first and second porous edge films facing the cathode and defining a first and second respective cathode and separator interface, the first and second porous edge film further wrapped around and onto an opposed second cathode surfaces with the first porous edge film disposed against the separator, wherein the first porous edge film protects the separator from contacting a conductive surface of the cathode along the first edge of the cathode and protects the cathode from tearing the separator and contacting the anode;
a battery case having a first opening sized for passage of the anode, the cathode, the separator, and the first and second porous edge films, the battery case having a feedthrough and an electrolyte backfill port;
a battery case lid sealably conformed to the first opening of the battery case;
pulse generation electronics electrically connected to the anode and the cathode; and
a hermetically sealed device housing having a device housing opening sized for passage of the battery case and the pulse generation electronics, with a housing lid sealably conformed to the device housing opening,
wherein a pressure sensitive adhesive interconnects the first and second porous edge films to the cathode along less than an entirety of the first and second cathode and separator interfaces wherein the pressure sensitive adhesive is disposed along the first porous edge film such that one or more areas of the first porous edge film are not covered with the pressure sensitive adhesive, wherein the anode, cathode, separator and first and second porous edge films are disposed in a jelly roll configuration in the battery case along with electrolyte, with the battery case and the pulse generation electronics disposed in the hermetically sealed device housing.

16. The apparatus of claim 15, wherein the first porous edge film has a porosity of approximately 55%.

17. The apparatus of claim 16, wherein the first porous edge film includes polyethylenetetrafluoroethylene.

* * * * *

UNITED STATES PATENT AND TRADEMARK OFFICE
CERTIFICATE OF CORRECTION

PATENT NO.       : 7,951,479 B2
APPLICATION NO.  : 11/127025
DATED            : May 31, 2011
INVENTOR(S)      : Shawn Kelley et al.

It is certified that error appears in the above-identified patent and that said Letters Patent is hereby corrected as shown below:

In column 10, line 22-25, in Claim 15, after "edges," delete "one or more surfaces of the first and second porous edge films facing the cathode and defining a first and second respective cathode and separator interface,".

In column 10, line 27, in Claim 15, delete "with" and insert -- defining a first and second respective cathode and separator interface, with --, therefor.

Signed and Sealed this
Fourth Day of October, 2011

David J. Kappos
*Director of the United States Patent and Trademark Office*